(12) United States Patent
Vitzthum et al.

(10) Patent No.: US 7,943,333 B2
(45) Date of Patent: May 17, 2011

(54) DIAGNOSTIC METHOD FOR IDENTIFYING CARRIERS OF THE MARBURG I VARIANT OF FACTOR VII-ACTIVATING PROTEASE (FSAP) ON THE BASIS OF DIFFERENTIAL MODULATION OF FSAP ACTIVITY

(75) Inventors: Frank Vitzthum, Lahntal-Sterzhausen (DE); Herbert Schwarz, Lohra (DE)

(73) Assignee: Siemens Healthcare Diagnostics Products GmbH, Marburg (DE)

( * ) Notice: Subject to any disclaimer, the term of this patent is extended or adjusted under 35 U.S.C. 154(b) by 692 days.

(21) Appl. No.: 11/642,747

(22) Filed: Dec. 21, 2006

(65) Prior Publication Data

US 2007/0190574 A1    Aug. 16, 2007

(30) Foreign Application Priority Data

Dec. 22, 2005  (DE) .................. 10 2005 062 053
Dec. 22, 2005  (DE) .................. 10 2005 062 055

(51) Int. Cl.
  *C12Q 1/37*  (2006.01)
  *C12Q 1/56*  (2006.01)
  *G01N 33/573*  (2006.01)
  *G01N 33/86*  (2006.01)

(52) U.S. Cl. ........... 435/7.4; 435/13; 435/23; 435/24; 436/69

(58) Field of Classification Search .............. None
See application file for complete search history.

(56) References Cited

U.S. PATENT DOCUMENTS

| | | | |
|---|---|---|---|
| 7,622,558 B2 * | 11/2009 | Schwarz et al. | 530/387.9 |
| 2002/0110552 A1 | 8/2002 | Romisch et al. | |
| 2002/0142316 A1 | 10/2002 | Roemisch et al. | |
| 2003/0124622 A1 * | 7/2003 | Roemisch et al. | 435/7.4 |
| 2003/0215447 A1 | 11/2003 | Roemisch et al. | |
| 2006/0045879 A1 | 3/2006 | Althaus et al. | |

FOREIGN PATENT DOCUMENTS

EP    0 952 215 A2    10/1999

OTHER PUBLICATIONS

J. Roemisch et al., "The frequent *Marburg* I polymorphism impairs the pro-urokinase activating potency of the factor VII activating protease (FSAP)," *Blood Coag. and Fibrinol.*, 13:433-441(2002).
J. Roemisch et al., "Quantitation of the Factor VII- and single-chain plasminogen activator-activating protease in plasmas of healthy subjects," *Blood Coag. and Fibrinol.*, 12: 375-383 (2001).
J. Roemisch et al., "Factor VII Activating Protease (FSAP): A Novel Protease in Hemostasis," *Biol. Chem.*, 383: 1119-1124 (2002).
J. Willeit et al., "Marburg I Polymorphism of Factor VII-Activating Protease: A Prominent Risk Predictor of Carotid Stenosis," *Circulation* 107: 667-670 (2003).
J. Romisch et al., "The FVII Activating Protease Cleaves Single-Chain Plasminogen Activators," *Haemostasis* 29: 292-299 (1999).
A. Hunfeld et al., "Detection of a Novel Plasma Serine Protease During Purification of Vitamin K-dependent Coagulation Factors," *FEBS Letters* 456: 290-294 (1999).

* cited by examiner

*Primary Examiner* — David A Saunders
(74) *Attorney, Agent, or Firm* — Finnegan, Henderson, Farabow, Garrett & Dunner, L.L.P.

(57) ABSTRACT

The present invention relates to a diagnostic method for identifying persons with genetically related hetero- or homozygous expression of the MR I variant of factor VII-activating protease (FSAP). The heterozygous or homozygous presence of an MR I polymorphism can be identified by a differential modulation of the FSAP activity.

19 Claims, 6 Drawing Sheets

Figure 1:
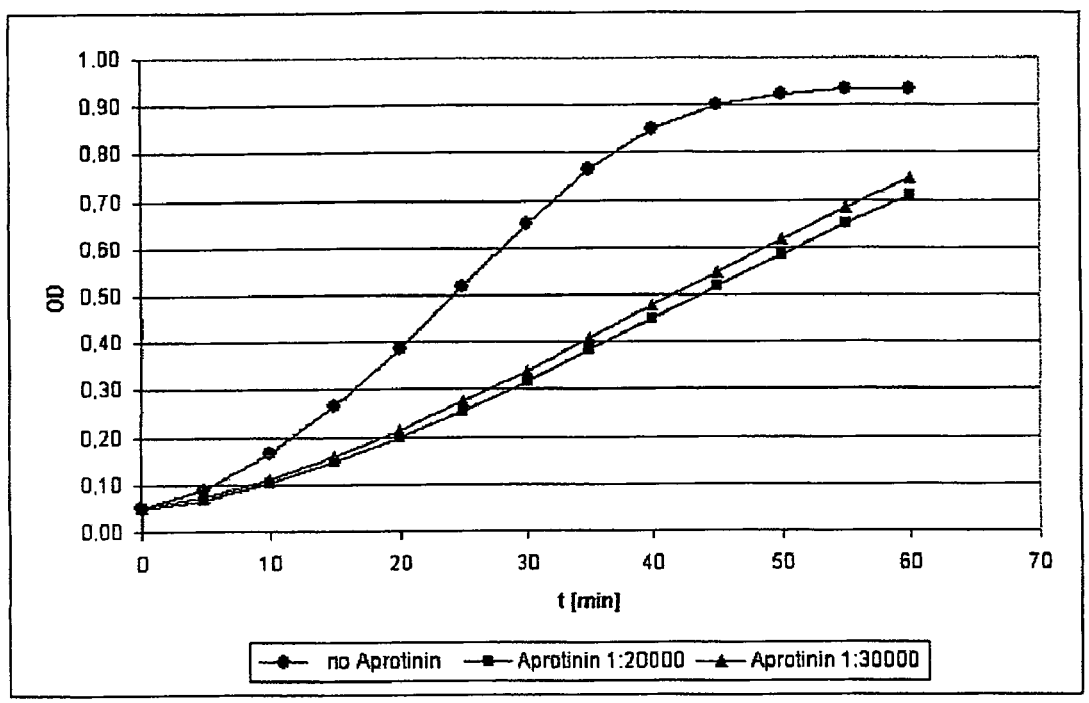

DIAGNOSTIC METHOD FOR IDENTIFYING CARRIERS OF THE MARBURG I VARIANT OF FACTOR VII-ACTIVATING PROTEASE (FSAP) ON THE BASIS OF DIFFERENTIAL MODULATION OF FSAP ACTIVITY

The invention relates to the area of the diagnosis of the Marburg I (MR I) mutation of the coagulation factor VII-activating protease (FSAP) which is found in approximately 5 to 10% of the West European population. According to a study by Willeit et al., heterozygous carriers of the FSAP MR I mutation have a higher risk than the average population of developing a carotid stenosis [Willeit et al. (2003): Marburg I polymorphism of factor VII-activating protease: a prominent risk predictor of carotid stenosis. Circulation 107, 667-670]. Since the presence of an FSAP MR I mutation represents a potential marker of a genetic predisposition to the development of atherosclerotic disorders, reliable identification of homo- or heterozygous carriers of the FSAP MR I mutation is of particular interest in relation to individual preservation of health.

FSAP is a plasma serine protease which has also been described under the name PHBSP (plasma hyaluronan binding serine protease). FSAP is present in human plasma in a concentration of about 12 μg/ml and can be converted via autocatalysis from the single-chain proenzyme (single chain-, sc-FSAP) into the active two-chain protease (two-chain-, tc-FSAP). The active protease has various functions and activities. It is known that FSAP has on the one hand the ability to activate coagulation factor VII and single-chain plasminogen activators such as plasminogen-activating prourokinases such as scuPA (single chain urokinase plasminogen activator) and sctPA (single chain tissue plasminogen activator). On the other hand, FSAP has the ability to inactivate coagulation factors V/Va and VIII/VIIIa.

Various test methods for the qualitative or quantitative determination of FSAP which make use of these biological activities of FSAP are described in EP 952 215 A2. A further activity of FSAP which makes it possible to determine the active protease and is likewise described in the aforementioned patent document and in Römisch et al. (1999): The FVII activating protease cleaves single-chain plasminogen activators. Haemostasis 29, 292-299, and in Hunfeld et al. (1999): Detection of a novel plasma serine protease during purification of vitamin K-dependent coagulation factors. FEBS Letters 456, 290-294, is the amidolytic activity of FSAP in relation to low molecular weight substrates, especially in relation to the chromogenic substrate S-2288 (HD-Ile-Pro-Arg-pNA).

Besides the wild-type sequence of the human FSAP gene, various nucleotide polymorphisms are known, and in two cases lead to an alteration of the amino acid sequence (EP 1 182 258 A1). The so-called Marburg I mutation (also Marburg I polymorphism, allele or variant) leads to a Gly/Glu amino acid exchange at position 534 of the proenzyme including the signal peptide (Gly/Glu 534) and results in a 50-80% reduction in the prourokinase-activating activity, whereas the ability to activate factor VII remains unchanged. A further mutation, called the Marburg II (MR II) mutation (also MR II polymorphism, allele or variant) leads to a Glu/Gln amino acid exchange at position 370 of the proenzyme including the signal peptide (Glu/Gln 370). The Marburg II mutation has, however, no influence on the prourokinase-activating activity of FSAP.

Persons carrying at least one copy of the FSAP MR I variant can be identified according to the prior art by means of two different methodological approaches. Reliable detection of the Gly/Glu amino acid exchange at position 534 of the proenzyme (Gly/Glu 534) is at present possible only by sequencing the corresponding coding region in the genomic DNA or the mRNA. A G/A base exchange in the genomic sequence which can be detected at nucleotide position 1601 in the cDNA forms the genetic cause of the FSAP MR I mutant (EP 1 182 258 A1). Even if the DNA sequence analysis provides reliable results, routine laboratories have a need for test methods which are as cost-effective, rapid and reliable as possible and which additionally can be performed automatically in available diagnostic apparatuses. The preference is chiefly for immunochemical detection and test methods because they satisfy the stated criteria and are already widely used in laboratory diagnostic procedures.

Another method for determining an FSAP MR I mutant is based on determining the prourokinase-activating potential of FSAP in a sample. For this purpose, a specific antibody which is unable to distinguish between wild-type FSAP and the known FSAP variants is coupled to a solid phase and incubated with the sample fluid. After addition of prourokinase as FSAP substrate and of a chromogenic urokinase substrate, the amount of converted chromogen is determined as a measure of the prourokinase-activating activity of FSAP. Carriers of the Marburg I mutation exhibit a prourokinase-activating activity which is reduced by 50-80%. However, a diminished prourokinase-activating activity may also be caused by a low FSAP concentration in the sample. It has therefore been necessary to date to determine not only the prourokinase-activating activity but additionally also the FSAP antigen concentration in a sample (EP 1 348 761 A1). Monoclonal antibodies which make it possible to detect FSAP immunologically are known in the art. EP 1 182 258 A1 describes two monoclonal antibodies which are derived from the hybridoma cell lines DSM ACC2453 and DSM ACC2454, which were obtained following immunization of mice with FSAP protein. Both antibodies bind not only the FSAP wild-type protein but also the Marburg I and II variants. Further known FSAP antibodies bind to equal extents to wild-type FSAP and to the known mutant variants, so that the total content of FSAP antigen in a sample is determined for example in a sandwich ELISA (see also DE 100 23 923 A1). The prior art therefore teaches that the presence of an FSAP MR I variant is specifically indicated only when a diminished prourokinase-activating activity is found together with an FSAP antigen concentration in the normal range.

The present invention was based on the object of providing further methods for reliable diagnosis of an MR I mutation and for identifying heterozygous or homozygous carriers of an MR I mutation, which make it possible to dispense with an FSAP antigen determination.

This object is achieved by providing the methods of the invention described in the claims, which make it possible to distinguish heterozygous or homozygous carriers of an MR I polymorphism reliably from non-carriers. The advantage of the present method, which makes use of the differential modulation of the activity of the FSAP MR I variant, consists of reliable discrimination between carriers and non-carriers of the FSAP MR I mutation, and in particular, that it is possible to dispense with an additional determination of the antigen content in a sample.

It has been found that through the use of suitable activity modulators, called differential activity modulators, the activity of FSAP, especially the amidolytic activity of FSAP, in relation to low molecular weight peptide substrates, and the plasminogen activator-activating activity of FSAP is modulated in samples from non-carriers of an MR I polymorphism differently from the activity of FSAP in samples from heteroor homozygous carriers of an MR I polymorphism, so that it is possible to distinguish between non-carriers and carriers of an MR I polymorphism on the basis of the different extent of the modulation of the FSAP activity.

A differential activity modulator means in the context of the present invention a substance or a mixture of substances which either i) inhibits or enhances, but to a different extent, the activity of FSAP both in samples from carriers of the MR I variant of FSAP and in samples from non-carriers of the MR I variant of FSAP, or ii) inhibits the activity of FSAP in samples from carriers of the MR I variant of FSAP, and enhances it in samples from non-carriers of the MR I variant, or vice versa, or iii) enhances or inhibits the activity of FSAP in one of the sample types but brings about a negligible change in the FSAP activity in the other sample type.

Thus, a substance or a mixture of substances which is suitable for use as differential activity modulator is one which a) brings about a quantitative difference in the inhibition (reduction) or enhancement (increase) of the FSAP activity in samples from respectively non-carriers and carriers of the MR I variant of FSAP, i.e. the FSAP activity is for example increased or reduced in both sample types, but to a different extent, or b) brings about a qualitative difference in the modulation of the FSAP activity in samples from respectively non-carriers and carriers of the MR I variant of FSAP, i.e. the activity is enhanced, i.e. increased, in one of the sample types, as the activity is diminished, i.e. inhibited, in the other sample type.

Figure 6:
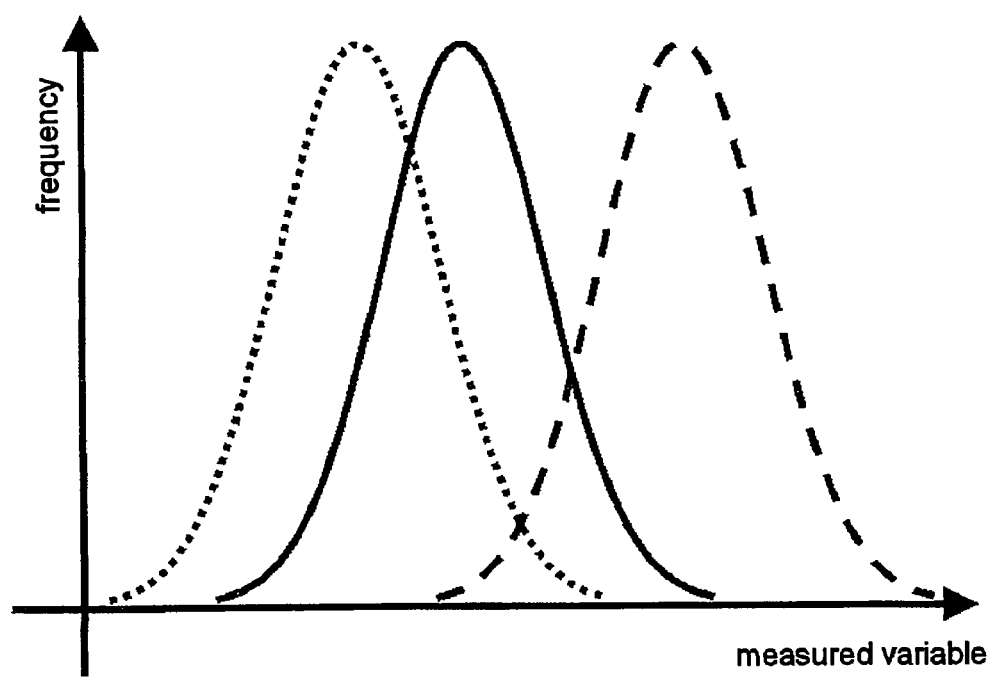

The different (differential) modulation of the FSAP activity in samples from carriers and non-carriers of the FSAP MR I variant makes a better differentiation of the two sample types possible. As depicted in FIG. 6, this leads to a reduction in the overlap of the distributions of the FSAP activities of samples from groups of non-carriers and carriers of the MR I polymorphism. It is thus possible to differentiate better between non-carriers and the various carriers, so that the diagnostic sensitivity and/or specificity is increased [Vitzthum, F. et al. (2005) Proteomics: from basic research to diagnostic application. A review of requirements & needs. J. Proteome Res. 4(4): 1086-97].

For example, on use of aprotinin as differential activity modulator, a quantitative difference is observed: the plasminogen activator-activating activity of FSAP in samples from non-carriers is inhibited more strongly than the plasminogen activator-activating activity of FSAP in samples from carriers of the FSAP MR I mutation. Homozygous and heterozygous carriers of the wild-type form and of the MR I variant of FSAP can thus be differentiated from one another and therefore identified.

The present invention therefore relates to an in vitro diagnostic method for identifying persons with genetically related hetero- or homozygous expression of the MR I variant of FSAP, wherein the extent of the change in the FSAP activity present in the sample is determined. For this purpose, the FSAP activity present in a sample is determined in the absence and in the presence of a differential activity modulator, it being possible to carry out the determination of the FSAP activity in the absence and in the presence either 1) in parallel, i.e. in two separate reaction mixtures, or 2) in succession, i.e. consecutively in a single reaction mixture first in the absence and, subsequent to the addition of the differential activity modulator, in the presence of the differential activity modulator.

It is possible to differentiate two preferred test principles suitable for determining the extent of the change in the FSAP activity:

1. Determination of the Change of Activity in Two Reaction Mixtures

In this test principle, the extent of the change in the FSAP activity present in a sample is determined by measuring the FSAP activity in a first reaction mixture, i.e. in a first aliquot of a sample, in the presence of a differential activity modulator of the FSAP activity, and measuring the FSAP activity in a second reaction mixture, i.e. in a second aliquot of the same sample, in the absence of this differential activity modulator. Comparison of the results of the two reactions provides information about the extent of the change of the FSAP activity in the presence of the activity modulator.

It is preferred to determine the extent of the change of the plasminogen activator-activating activity of FSAP in a biological sample, preferably a blood or plasma sample, by measuring the prourokinase-activating activity of FSAP once in the absence and once in the presence of a differential activity modulator on the basis of the kinetics of reaction of a plasminogen activator and its substrate.

In another embodiment, the extent of the change of the amidolytic activity of FSAP in a biological sample, preferably a blood or plasma sample, is determined by measuring the amidolytic activity of FSAP once in the absence and once in the presence of a differential activity modulator on the basis of the kinetics of reaction of a low molecular weight FSAP substrate.

2. Determination of the Change in Activity in a Single Reaction Mixture

In this test principle, the extent of the change in the FSAP activity present in a sample is determined by incubating the sample with one or more reagents which allow the FSAP activity to be determined in a single reaction mixture, and with addition of a differential activity modulator during the reaction, and following the resulting change in the reaction.

It is preferred to determine the extent of the change in the plasminogen activator-activating activity of FSAP in a biological sample, preferably a blood or plasma sample, by measuring the prourokinase-activating activity of FSAP first in the absence of a differential activity modulator on the basis of the kinetics of reaction of a plasminogen activator substrate or of a urokinase substrate. Then, during the reaction, a differential activity modulator is added to the reaction mixture, and the resulting change in the reaction is followed.

In another embodiment, the extent of the change in the amidolytic activity of FSAP in a biological sample, preferably a blood or plasma sample, is determined by measuring the amidolytic activity of FSAP first in the absence of a differential activity modulator on the basis of the kinetics of reaction of a low molecular weight FSAP substrate. Then, during the reaction, a differential activity modulator is added to the reaction mixture, and the resulting change in the reaction is followed.

A "sample" means in the context of the invention a material which is presumed to contain the FSAP or FSAP MR I variant. The term "sample" includes biological fluids or tissues, in particular from humans and animals, such as blood, plasma, serum and other body fluids, excreta or extracts which are presumed to contain the FSAP or FSAP MR I mutant. Pretreatment of the samples is necessary where appropriate in order to make the analytes available for the detection method or in order to remove interfering sample constituents. Such pretreatment of samples may comprise the removal and/or lysis of cells, the precipitation, the hydrolysis or the denaturation of sample constituents such as, for example, proteins, the centrifugation of samples, the treatment of the sample with organic solvents such as, for example, alcohols, especially methanol, the treatment of the same with detergents. The sample is frequently transferred into a different, usually aqueous, medium which ought to interfere as little as possible with the detection method.

In a preferred embodiment for determining the FSAP activity, a biological sample, preferably a blood or plasma sample, is incubated with a solid phase onto which a binding partner having affinity for FSAP has previously been coupled. Preference is to be given to binding partners which bind wild-type FSAP protein with the same affinity as an FSAP protein with MR I mutation. Binding partners which exhibit an affinity for FSAP and are suitable for enriching or isolating FSAP protein from complex protein solutions such as, for example, plasma samples are, for example, substances from the group of heparin, heparan sulfate, dextran sulfate and hyaluronic acid. Likewise suitable are monoclonal or polyclonal antibodies against FSAP or antibody fragments such as F(ab') or F(ab')$_2$ fragments. Particular preference is given to monoclonal antibodies produced by one of the hybridoma cell lines DSM ACC2453 and DSM ACC2454, which are deposited with the DSMZ—Deutsche Sammlung von Mikroorganismen und Zellkulturen GmbH, MascheroderWeg 1b, 38124 Braunschweig (Brunswick), Germany.

The term "solid phase" in the context of this invention comprises an article which consists of a porous and/or non-porous, usually water-insoluble material and which may have a wide variety of shapes, such as, for example, that of vessels, tubes, microtiter plates, beads, microparticles, rods, strips, filter paper or chromatography paper. The surface of the solid phase is usually hydrophilic or can be made hydrophilic. The solid phase may consist of a wide variety of materials such as, for example, of inorganic and/or of organic materials, of synthetic, of naturally occurring and/or of modified naturally occurring materials. Examples of solid-phase materials are polymers such as, for example, cellulose, nitrocellulose, cellulose acetate, polyvinyl chloride, polyacrylamide, crosslinked dextran molecules, agarose, polystyrene, polyethylene, polypropylene, polymethacrylate or nylon, ceramic, glass, metals, especially noble metals such as gold and silver; magnetite, mixtures or combinations thereof etc. The solid phase may have a coating of one or more layers, e.g. of proteins, carbohydrates, lipophilic substances, biopolymers, organic polymers or mixtures thereof, in order for example to reduce or prevent nonspecific binding of sample constituents to the solid phase or in order for example to achieve improvements in relation to the suspension stability of particulate solid phases, the storage stability, the shaping stability or the resistance to UV light, microbes or other agents having a destructive effect. Microparticles are frequently used as solid phase. The term "microparticles" means in the context of this invention particles which have an approximate diameter of at least 20 nm and not more than 20 µm, normally between 40 nm and 10 µm, preferably between 0.1 and 10 µm, particularly preferably between 0.1 and 5 µm, very particularly preferably between 0.15 and 2 µm. The microparticles may have regular or irregular shapes. They may represent spheres, spheroids, spheres with larger or smaller cavities or pores. The microparticles may consist of organic, of inorganic material or of a mixture or combination of the two. They may consist of a porous or non-porous, of a swellable or non-swellable material. It is possible in principle for the microparticles to have any density. The microparticles may consist of a plurality of layers such as, for example, the so-called core and shell particles having a core and one or more enveloping layers. The term microparticles includes for example dye crystals, metal soles, silica particles, glass particles, magnetic particles, polymer particles, oil drops, lipid particles, dextran and protein aggregates, particles consisting of polymeric material, in particular of substituted polyethylenes, latex particles, e.g. of polystyrene, acrylic acid polymers, methacrylic acid polymers, acrylonitrile polymers, acrylonitrile-butadiene-styrene, polyvinyl acetate-acrylate, polyvinylpyridine, vinyl chloride-acrylate. Particles of particular interest have reactive groups on their surface such as, for example, carboxyl, amino or aldehyde groups, which allow covalent bonding for example of binding partners to the latex particles.

The plasminogen activator-activating activity of FSAP is determined, after washing out the solid phase, by incubating the FSAP bound to the binding partner with an inactive single-chain plasminogen activator such as, for example, prourokinase or sct-PA and a urokinase substrate or an sct-PA substrate. The FSAP-dependent activation of, for example, prourokinase to urokinase is measured on the basis of the conversion or cleavage of the urokinase substrate. Preferred substrates are low molecular weight peptide substrates which have a signal-generating group. Cleavage of the substrate leads to release of the signal-generating group. The physical or chemical properties of the released signal-generating group differ from the properties of the group coupled to the peptide and can be determined quantitatively with the aid of suitable methods. Examples of a suitable signal-forming group are the luminophores, fluorophores or chromophores which are known to the skilled person and can be measured by means of optical methods such as, for example, luminescence, fluorescence or absorption measurements. Since the strength of the signal correlates with the amount of cleaved substrate, it is thus possible to determine the plasminogen activator-activating activity of FSAP. It is preferred to use a low molecular weight substrate from the group of S-2444 (Glu-Gly-Arg-para-nitroaniline; Chromogenix Instrumentation Laboratory S.p.A., Milano, Italy), Pefachrome® uPA (Ala-Gly-Arg-para-nitroaniline [Pefa-5221]; Pentapharm Ltd., Basle, Switzerland) and Chromozym U (Roche Applied Science, Indianapolis, USA).

The amidolytic activity of FSAP is determined, after washing the solid phase, by incubating the FSAP bound to the binding partners with a low molecular weight substrate, and measuring the conversion or cleavage of the substrate. Low molecular weight substrates in the context of the present invention are peptide substrates consisting of a sequence of from 2 to 100, preferably 2 to 50, particularly preferably 3 to 10, natural or unnatural amino acids, which additionally have a signal-generating group and which are cleaved by FSAP. Cleavage of a low molecular weight substrate leads to release of the signal-generating group. The physical or chemical properties of the released signal-generating group differ from the properties of the group coupled to the peptide and can be determined quantitatively with the aid of suitable methods. Examples of a suitable signal-generating group are the luminophores, fluorophores or chromophores which are known to the skilled person and can be measured by means of optical methods such as, for example, luminescence, fluorescence or absorption measurements. Since the strength of the signal correlates with the amount of cleaved substrate, it is thus possible to determine the amidolytic activity of FSAP. It is preferred to use a low molecular weight chromogenic substrate from the group of Pefa-3297, Pefa-5114, Pefa-5523, Pefa-5773, Pefa-5979, Pefa-3107, Pefa-5329 (all from the Pefachrom series, Pentapharm Ltd., Basle, Switzerland), S-2288, S-2765, S-2366, S-2238, S-2222, S-2302 (all from the S series, Chromogenix Instrumentation Laboratory S.p.A., Milano, Italy) [see also Römisch et al. (1999) Haemostasis 29, 292-299 and Hunfeld et al. (1999) FEBS Letters 456, 290-294].

Measurement of the substrate-cleavage reaction can take place over the complete time interval of the reaction until equilibrium is set up or in at least one defined time interval or at least at one point in time. The activity can be determined by using the photometric data, for example spectra or absorption values at defined wavelengths, as such or in relation to a time interval. If the activity is determined by photometric data in relation to a time interval, i.e. the conversion or reaction rate is ascertained, it is possible to employ various methods for determining the conversion or reaction rate. For example, the conversion rate can be determined by means of time-conversion plots. In time-conversion plots, the cleavage product concentration is plotted against time. To determine the conversion rate, a straight line is fitted in the range of the zero order reaction in the time-conversion plot, normally at the start of a measurement of an enzymic reaction. The slope of the straight line then provides the conversion rate, i.e. the change in concentration of the substrate or product in a defined time interval [literature: Bisswanger, H., Enzymkinetik: Theorie und Methoden, $2^{nd}$ completely revised edition, VCH Verlagsgesellschaft mbH, 1994, Weinheim, N.Y., Basle, Cambridge, Tokyo; in particular pages 66-67].

Measured variables or parameters suitable for evaluating the kinetics of a reaction are, for example, all parameters which describe the reaction kinetics, such as, for example, curve sketching per se, but especially individual parameters of the reaction kinetics such as the maximum slope, i.e. the reaction rate ($v_{max}$), sigmoidity parameters, linearity parameters, the area under the curve, etc. Examples of parameters suitable for test evaluation are also absolute measurement readings such as, for example, absorptions measured at a defined time, or a time at which a defined absorption, e.g. a maximum, is reached.

In the determination of the FSAP activity change in two reaction mixtures, preferably the difference or the quotient of a test parameter which has been determined once in the absence and once in the presence of the activity modulator is formed in order to determine the extent of the change in the FSAP activity. When an inhibitor which inhibits the FSAP activity in samples from non-carriers more strongly than in samples from MR I carriers is used it is possible to differentiate FSAP MR I carriers and non-carriers for example by forming the difference or the quotient of the reaction rate ($v_{max}$) of the substrate conversion rate in the absence of the inhibitor ($v_{max0}$) and the reaction rate of the substrate conversion rate in the presence of the inhibitor ($v_{max\ inhibitor}$). Homozygous and heterozygous carriers of the FSAP MR I mutation exhibit respectively a smaller difference and a lower quotient than non-carriers. Other algorithms such as the total or the product are likewise suitable if they allow differentiation.

Figure 2:
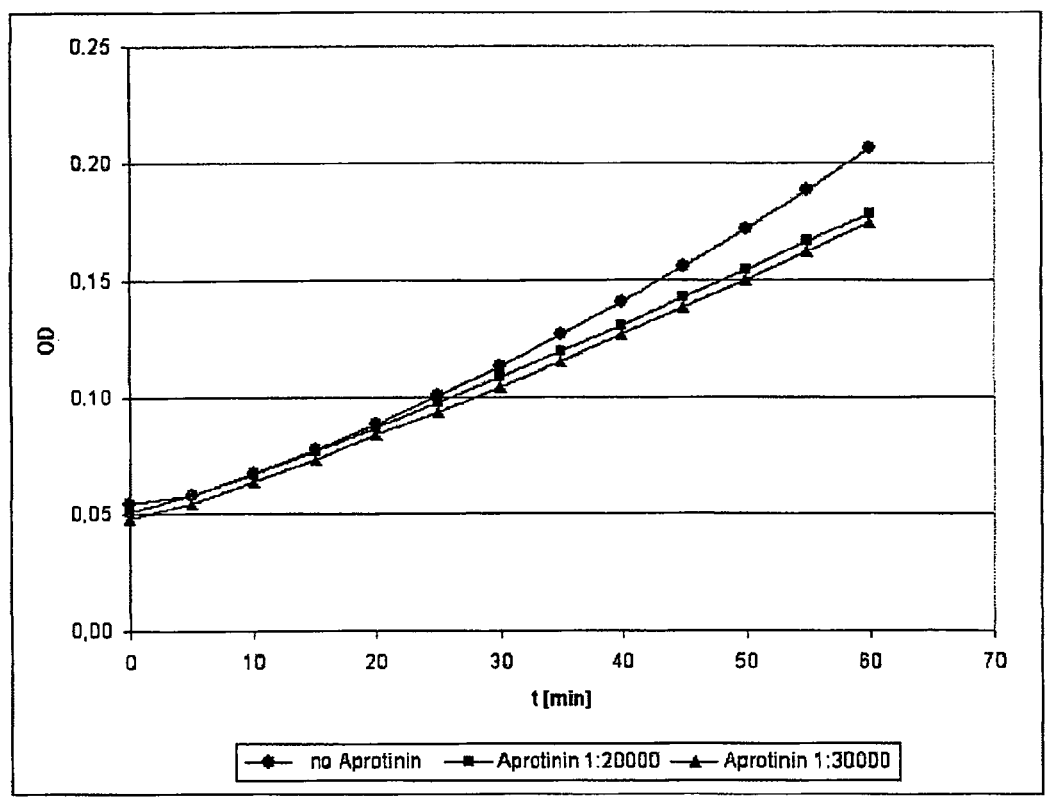

Besides the reaction rate, it is also possible to use absolute test signals or measurement readings such as, for example, absorptions that are reached at a defined time (cf. for example, FIGS. 1 and 2: a suitable time in this case might be fixed preferably in a time interval between 10 and 70 min, particularly preferably between 30 and 45 min, especially at 40 min, because a maximum difference between the mixtures with and without aprotinin exists here).

When the FSAP activity change is determined in a single reaction mixture it is necessary to measure the substrate cleavage reaction before and after addition of the differential activity modulator. It is necessary at least to measure the reaction at least at one time or over a discrete time interval before and at least at one time or over a discrete time interval after addition of the differential activity modulator.

A preferred differential activity modulator of FSAP activity for use in the method of the invention is aprotinin. Aprotinin inhibits the FSAP activity in samples from non-carriers more strongly than in samples from MR I carriers (see table 3).

Further preferred differential activity modulators of FSAP activity for use in the method of the invention are monoclonal or polyclonal anti-FSAP antibodies. Particularly preferred monoclonal antibodies are those produced by one of the hybridoma cell lines deposited under the deposit numbers DSM ACC2454 (EP 1 182 258 A1), DSM ACC2726 and DSM ACC2674 (both EP 1 630 175 A1) at the Deutsche Sammlung von Mikroorganismen und Zellkulturen GmbH, MascheroderWeg 1b, 38124 Brunswick, Germany. Likewise preferred are monoclonal anti-FSAP antibodies which bind to an epitope of FSAP which is bound by one or more of the antibodies just mentioned, which are produced by one of the hybridoma cell lines DSM ACC2454, DSM ACC2726 and DSM ACC2674. These monoclonal antibodies bind to the FSAP and modulate the FSAP activity in samples from non-carriers to a different extent than in samples from MR I carriers (see table 3).

A possible method for establishing whether a substance or a combination of substances is suitable for use as differential activity modulator in the context of the present invention is as follows:

The influence of the substance to be investigated or of the combination of substances to be investigated on the plasminogen activator-activating activity of FSAP is determined using samples which are known to contain the FSAP MR I variant and with samples which are known not to contain the FSAP MR I variant but contain the FSAP wild-type form. The samples in this connection may be for example from one or more persons whose FSAP genotype is known. It is additionally possible to use samples which contain a defined amount of FSAP wild-type protein or FSAP MR I protein. The FSAP protein or the FSAP MR I protein which can be used to prepare such a sample may be for example enriched or isolated from human biological material or be prepared recombinantly or transgenically. Methods for the enrichment, isolation, preparation or stabilization of FSAP protein are described for example in the documents EP 1 226 829 A2, EP 1 074 615 A1 and EP 1 074 616 A1.

The plasminogen activator-activating activity of FSAP which is present in the various samples is then determined in the absence and in the presence of the substance to be investigated. The substance or the combination of substances which is to be investigated for its suitability as differential activity modulator are in this case employed in at least one concentration, but preferably in various concentrations, as depicted by way of example for aprotinin in FIGS. 1 and 2.

The extent of the change in the plasminogen activator-activating activity of FSAP of samples having the FSAP MR I variant compared with samples not containing the FSAP MR I variant but showing activity of the FSAP wild-type form allows the identification of substances or combinations of substances which can be used as differential activity modulators. It is possible in this connection to identify substances as differential activity modulators by their inhibition or enhancement, but to differing extents, of both the activity of the FSAP MR I variant and of the activity of the FSAP wild-type form. However, a substance is also a differential activity modulator if it inhibits the activity of the FSAP MR I variant and enhances the activity of the FSAP wild-type form, or vice versa.

Initial investigations of whether substances are suitable as differential modulators are carried out with a comparatively small number of samples, for example with in each case at least one sample of the FSAP MR I variant, but preferably with in each case 2 to 10 samples. Substances which in this case afford a significant, preferably a statistically significant, differentiation of samples with FSAP wild type and FSAP MR I can be validated by further investigations with larger numbers of samples.

The tests employed for further validation of substances or combinations of substances preferably use samples from persons with a known genotype in order to obtain realistic information about the efficiency of the test for determining the presence or the absence of an FSAP MR I variant with sufficient diagnostic specificity and sensitivity. The number of samples to be investigated in such a phase I study depends on the accuracy to be expected for the test and on the ratio of the number of samples with and without FSAP MR I variant [Obuchowski, N. A. et al. (2004) ROC Curves in Clinical Chemistry: Uses, Misuses and Possible Solutions, Clinical Chemistry, 50:7, 1118-1125]. If the accuracy of the test is almost perfect and the ratio of samples with and without FSAP MR I variant is equal to one, ten samples are sufficient in each case in order to obtain statistically significant values. The number of samples increases as the ratio of the samples with and without FSAP MR I variant increases and decreases, and as the accuracy of the test decreases. It is necessary in this case for example to investigate more than a hundred samples in each case.

Investigation of substances or combinations of substances in relation to their suitability as differential activity modulators can take place for example by determining the prourokinase-activating activity of FSAP in the presence and absence of these substances, where appropriate in various concentrations. For example, solid phase-associated binding partners having affinity for FSAP, in particular an anti-FSAP antibody which is produced by the hybridoma cell line DSM ACC2453, are used as in example 1, and an activity assay is carried out as described in example 1. Differentiation between carriers and non-carriers of the FSAP MR I variant is determined by forming a quotient between $v_{max}$ of the reaction kinetics of a sample without the addition ($v_{max0}$) and with the addition of substance ($v_{max\ substance}$).

An analogous procedure is possible if the intention is to investigate substances or combinations of substances in relation to their suitability as differential activity modulators of the amidolytic activity of FSAP. A test method for determining the amidolytic activity of FSAP as described in example 2 can be carried out once in the absence and once in the presence of the substance to be investigated, and the test results can be used in an analogous manner for assessing the suitability of a substance as just described.

Examples of classes of substances particularly suitable for investigation for their suitability as differential activity modulators of FSAP activity are:

a) ions (anions such as chloride, carbonate, sulfate, phosphate etc. or cations such as sodium, lithium, ammonium, magnesium, calcium, manganese etc.);
b) chelators such as ethylenediaminetetraacetate (EDTA), ethylene glycol bis(β-aminoethyl ether)-N,N,N',N'-tetraacetate, citrate etc.;
c) detergents such as sodium dodecyl sulfate (SDS), Triton® X 100, Tween® etc.;
d) redox-active substances such as dithioerythrol, dithiothreitol, β-mercaptoethanol, glutathione, lipoic acid, vitamin C, vitamin E etc.;
e) nucleic acids, especially aptamers;
f) antibodies;
g) proteins, peptides and oligopeptides such as, for example, antithrombin III, C1-esterase inhibitor, tissue factor pathway inhibitor (TFPI), heparin cofactor II, alpha2-macroglobulin, alpha2-antiplasmin, inter-alpha-trypsin inhibitor, alpha1-antitrypsin, alpha1-antichymotrypsin, plasminogen activator inhibitor of type 2 (PAI-2), plasminogen activator inhibitor of type 3 (PAI-3), kininogen, high molecular weight kininogen (HMWK) etc.;
h) synthetic serine protease inhibitors such as FOY-305 [N,N-dimethyl carbamoylmethyl 4-(4-guanidinobenzoyloxy) phenylacetate methane-sulfonate] and corresponding derivatives;
i) low molecular weight protease inhibitors such as FOIPAN (camostat mesilate).

FIGURES

FIG. 1

FIG. 1 shows the inhibition of the prourokinase-activating activity of FSAP in the presence of aprotinin, which was found for a plasma sample of a non-carrier (wild type).

FIG. 2

FIG. 2 shows the inhibition of the prourokinase-activating activity of FSAP in the presence of aprotinin, which was found for a plasma sample of a heterozygous carrier of the MR I polymorphism.

FIG. 3

Figure 3:
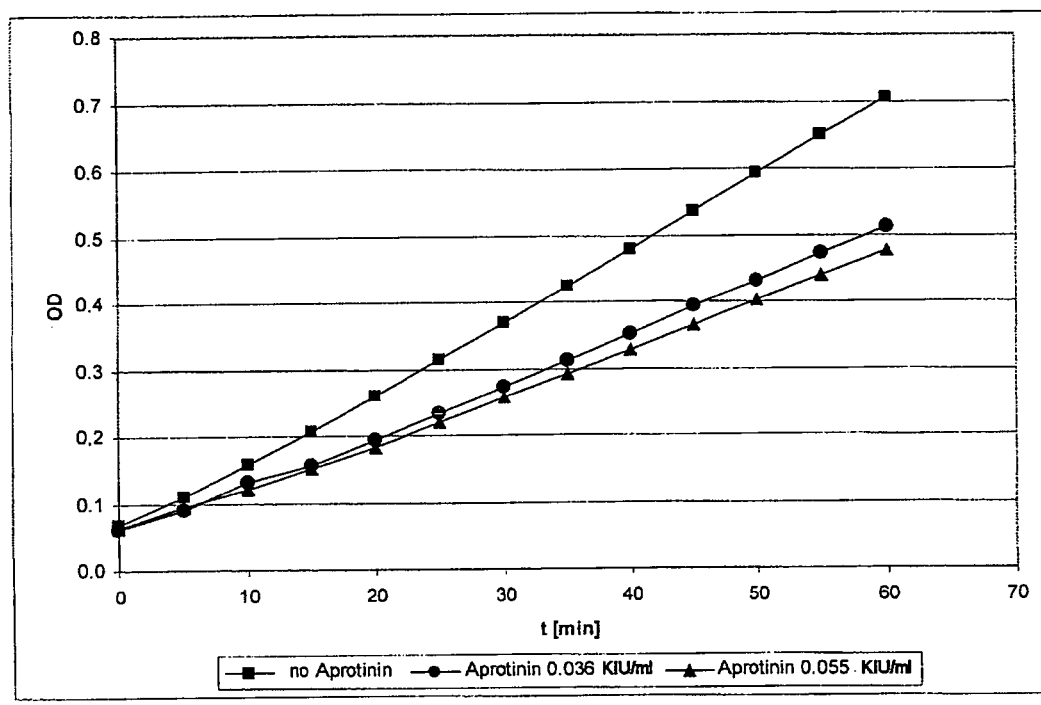

FIG. 3 shows the inhibition of the amidolytic activity of FSAP in the presence of aprotinin, which was found for a sample of a plasma pool of non-carriers of the FSAP MR I mutation (wild type).

FIG. 4

Figure 4:
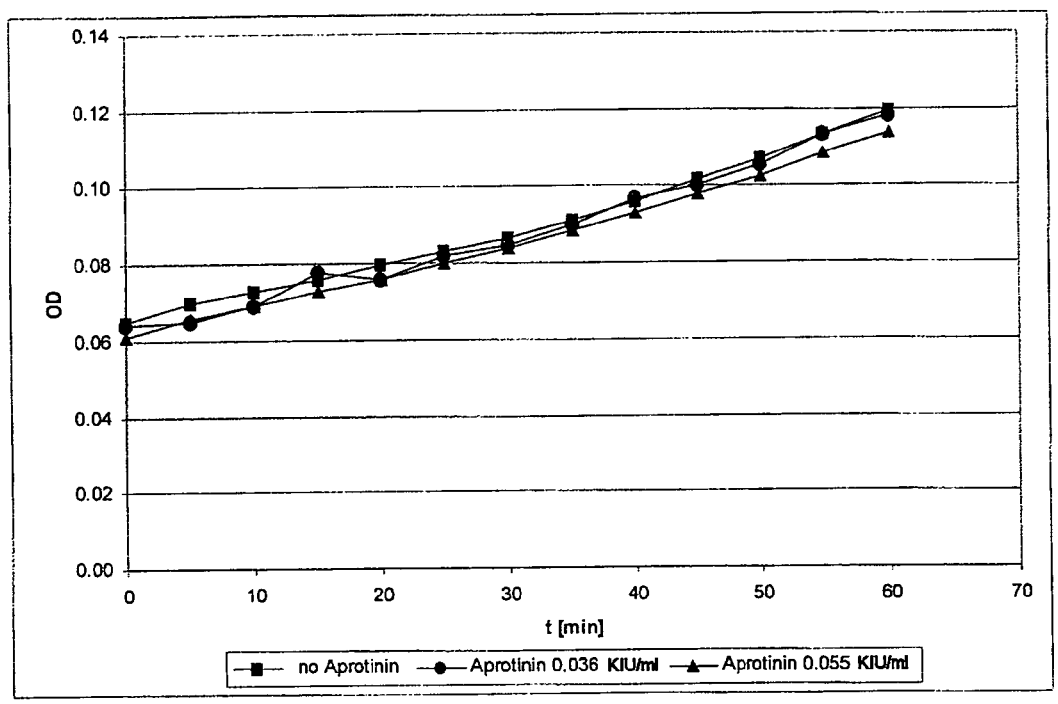

FIG. 4 shows the inhibition of amidolytic activity of FSAP in the presence of aprotinin, which was found for a plasma sample of a heterozygous carrier of the MR I polymorphism.

FIG. 5

Figure 5:
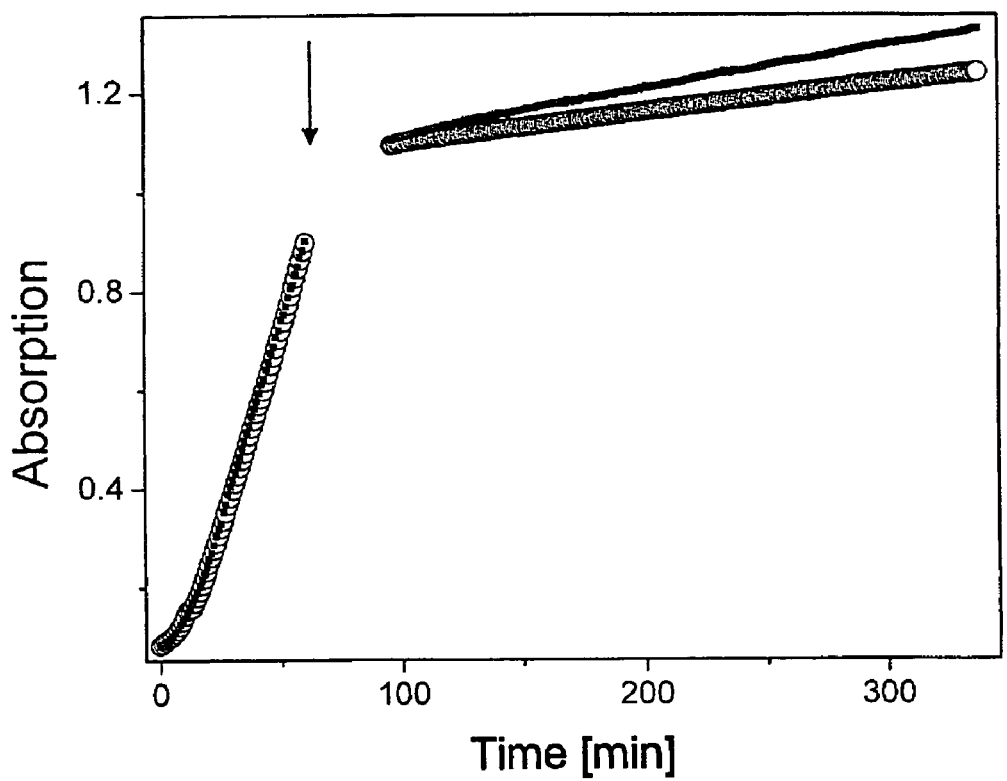

FIG. 5 shows the change in the amidolytic activity of FSAP for a plasma sample of a non-carrier (wild type; white circles) and of a heterozygous carrier of the MR I polymorphism (black squares) in the absence of aprotinin and in the presence of aprotinin after its addition (arrow) with a reaction time of about one hour, the activity having been measured in a single reaction mixture. Although both samples initially show the same FSAP activity in the absence of aprotinin, and thus no differentiation is possible, the activities change in the presence of aprotinin so that the two samples can be differentiated because the FSAP activity is inhibited more strongly in the sample of the non-carrier.

FIG. 6

FIG. 6 shows by way of example a possible frequency distribution of a measured variable such as, for example, the FSAP activity in samples from groups of homozygous carriers of the wild-type form (broken line) and of MR I heterozygotes (full and dotted lines). The modulator used in the case of the dotted line has no influence on the FSAP activity in homozygous carriers of the wild-type form but further reduces the FSAP activity in the MR I heterozygotes. The overlap of the distributions of the FSAP activities of samples from groups of carriers of the wild-type form and of MR I heterozygotes is less in the presence of the activity modulator than in its absence. A better differentiation between the various carriers and forms is thus possible in the presence of the activity modulator than in its absence, so that the diagnostic sensitivity and/or specificity is increased.

The examples described below serve for exemplary illustration of individual aspects of this invention and are not to be understood as restriction:

EXAMPLE 1

Determination of the Prourokinase-Activating Activity of FSAP in the Presence and in the Absence of the Differential Activity Modulator Aprotinin An anti-FSAP antibody produced via the hybridoma cell line DSM ACC2453 was used as solid phase-associated binding partner having affinity for FSAP. Polystyrene microtiter plates (MTPs) were used as solid phase for carrying out the heterogeneous detection method. Anti-FSAP antibodies in 50 mM NaHCO$_3$, pH 8.2, were associated onto the polystyrene solid phase with a coating volume of 120 µl per well of the MTP and a coating concentration of 20 µg of antibody per ml at room temperature overnight. Unbound antibodies were removed by washing three times with 50 mM sodium phosphate-buffered isotonic NaCl solution, 0.02% Tween® 20, pH 6.5.

In each case 100 µl of a plasma sample to be determined were pipetted in a dilution of 1:80 in sample buffer (20 mM sodium citrate, pH 6.0, with 150 mM NaCl, 100 mM L-arginine monohydrochloride, 1% bovine serum albumin, 0.1% Tweene® 80, 100 I.U. of heparin/ml) into the wells. After incubation at +37° C. for one hour, unbound constituents were removed by washing three times with 50 mM sodium phosphate-buffered isotonic NaCl solution, 0.02% Tweene® 20, pH 6.5.

To determine the prourokinase-activating activity of FSAP, after removal of the sample and washing out of the solid phase
a) 30 µl of test buffer I (50 mM tris/HCl, pH 7.2, with 150 mM NaCl, 0.2% Tween® 80, 15 mM CaCl2 and 50 I.U./ml heparin) or
b) 30 µl of test buffer I which additionally contains aprotinin in a concentration such that a final concentration of 0.055 KIU/ml aprotinin was achieved in the reaction mixture (1 U=1 kallikrein-inhibiting unit [KIU]; aprotinin from bovine lung, Sigma-Aldrich Laborchemikalien GmbH, Taufkirchen, Germany)
and in each case 50 µl of recombinant prourokinase (Landing Biotech Inc., Brighton, Mass., USA; 5 µg/ml in test buffer 1) and in each case 50 µl of the chromogenic substrate S-2444 (0.6 mM) in test buffer II (100 mM tris/HCl, 150 mM NaCl, 15 mM Na azide, 0.1% Tween® 80, pH 8.2) were put into an MTP well and incubated at +37° C. The change in absorption (OD) of the reaction mixtures was followed at a wavelength of 405 nm. The results are summarized in table 1. A differentiation between carriers and non-carriers of the FSAP MR I variant is possible through the formation of a quotient between vmax of the reaction kinetics of a sample without added aprotinin (vmax0) and with added aprotinin (vmax aprotinin). The following applies thereto:
FSAP wild type $v_{max0}$/FSAP wild type $v_{max\ aprotinin}$>FSAP MR I $v_{max0}$/FSAP MR I $v_{max\ aprotinin}$.

In addition, FSAP MR I samples (MR I) show a distinctly smaller difference between $v_{max0}$ and $v_{max\ aprotinin}$ than FSAP wild-type samples (WT) (see table 1). The average of the three individual determinations is shown in the Av. column.

The maximum slope of the time-conversion plots was determined by linear regression in a sufficiently linear region of the time-conversion plot and afforded the maximum reaction rate $v_{max}$ of a reaction in mOD/min.

TABLE 1

| Sample No. | FSAP | Without aprotinin $v_{max0}$ | 0.055 KIU/ml aprotinin $v_{max\ aprotinin}$ | $v_{max0}$/ $v_{max\ aprotinin}$ | Av. $v_{max0}$/ $v_{max\ aprotinin}$ | $v_{max0}$ − $v_{max\ aprotinin}$ | Av. $v_{max0}$ − $v_{max\ aprotinin}$ |
|---|---|---|---|---|---|---|---|
| 14942 | MR I | 3.04 | 2.00 | 1.52 | 1.43 | 1.04 | 0.90 |
| 229 | MR I | 2.48 | 1.84 | 1.35 | | 0.64 | |
| 808 | MR I | 3.45 | 2.45 | 1.41 | | 1.01 | |
| 2173 | WT | 23.07 | 11.84 | 1.95 | 2.01 | 11.23 | 11.37 |
| 2175 | WT | 26.23 | 13.82 | 1.90 | | 12.42 | |
| 2185 | WT | 21.47 | 12.09 | 1.78 | | 9.38 | |
| 2196 | WT | 21.25 | 8.81 | 2.41 | | 12.44 | |

FIGS. 1 and 2 show the different reaction kinetics of the conversion of S-2444, i.e. the prourokinase-activating activity of FSAP. FIG. 1 shows the reaction kinetics found for a plasma sample of a non-carrier without and with addition of aprotinin (0.036 and 0.055 KIU/ml, final aprotinin concentration). In this addition, 0.036 KIU/ml aprotinin corresponds to an aprotinin dilution of 1:30 000 and 0.055 KIU/ml corresponds to an aprotinin dilution of 1:20 000. FIG. 2 shows the reaction kinetics found for a plasma sample of a heterozygous carrier of the FSAP MR I variant without and with addition of aprotinin (0.036 and 0.055 KIU/ml final aprotinin concentration). It is clearly evident that the prourokinase-activating activity of FSAP in the sample of the non-carrier is inhibited in the presence of aprotinin substantially more strongly than the prourokinase-activating activity of FSAP in the sample of the heterozygous carrier.

EXAMPLE 2

Determination of the Amidolytic Activity of FSAP for the Low Molecular Weight Chromogenic Peptide Substrate S-2288 in the Presence and Absence of the Differential Activity Modulator Aprotinin The microtiter plates used were the same as described in example 1. In each case 100 µl of a plasma sample to be determined were pipetted in a dilution of 1:50 in sample buffer (see example 1) into the wells. After incubation at +37° C. for one hour, unbound constituents were removed by washing three times with 50 mM sodium phosphate-buffered isotonic NaCl solution, 0.02% Tweene® 20, pH 6.5.

To determine the amidolytic activity of FSAP, after removal of the sample and washing out of the solid phase
a) 30 µl of test buffer I (see example 1) or
b) 30 µl of test buffer I which additionally contained aprotinin in a concentration such that a final concentration of 0.055 KIU/ml aprotinin was reached in the reaction mixture (see example 1)
and in each case 80 µl of the chromogenic substrate S-2288 (1.5 mmol/L; Chromogenix Instrumentation Laboratory S.p.A., Milan, Italy) in test buffer II (see example 1) were put into the test well and incubated at 37° C. for one hour. In order to reduce evaporation effects during the relatively long incubation time in the MTP, a layer of mineral oil was put on top.

The change in absorption (OD) of the reaction mixtures was followed at a wavelength of 405 nm, and the maximum reaction rate $v_{max}$ was determined (see example 1). The results are summarized in table 2. Differentiation between carriers and non-carriers of the FSAP MR I variant is possible through the formation of a ratio (quotient) between $v_{max}$ of the reaction kinetics of a sample without added aprotinin ($v_{max0}$) and with added aprotinin ($v_{max\ aprotinin}$). The following applies thereto:
FSAP wild type $v_{max0}$/FSAP wild type $v_{max\ aprotinin}$>FSAP MR I $v_{max0}$/FSAP MR I $v_{max\ aprotinin}$.

In addition, FSAP MR I samples (MR I) show a distinctly smaller difference between $v_{max0}$ and $v_{max\ aprotinin}$ than in FSAP wild-type samples (WT) (see table 2). The average of the three individual determinations is shown in the Av. column.

of 2.95 KIU/ml or the respective monoclonal antibody (MAb) was added in a final concentration of about 60 µg/ml per reaction mixture. The change in absorption of the reaction mixtures was followed at a wavelength of 405 nm, and the maximum reaction rate $v_{max}$ was determined (see example 1). In order to reduce evaporation effects during the relatively long incubation time, a layer of mineral oil was put on top.

Differentiation between carriers and non-carriers of the FSAP MR I variant is possible through forming a ratio, for example the quotient of the maximum reaction rate before addition of the differential activity modulator ($v_{max}$) and the maximum reaction rate after addition of the differential activity modulator ($v_{max\ aprotinin}$).

As shown in FIG. 5, the following applies to the activity modulator aprotinin:
FSAP wild type $v_{max}$/FSAP wild type $v_{max\ aprotinin}$>FSAP MR I $v_{max0}$/FSAP MR I$_{vmax\ aprotinin}$.

Table 3 shows besides aprotinin also the influence of monoclonal antibodies (Mabs) on the quotient $v_{max}$/

TABLE 2

| Sample No. | FSAP | Without aprotinin $v_{max0}$ | 0.055 KIU/ml aprotinin $v_{max\ aprotinin}$ | $v_{max0}$/$v_{max\ aprotinin}$ | Av. $v_{max0}$/$v_{max\ aprotinin}$ | $v_{max0}$ − $v_{max\ aprotinin}$ | Av. $v_{max0}$ − $v_{max\ aprotinin}$ |
|---|---|---|---|---|---|---|---|
| 14942 | MR I | 1.24 | 1.22 | 1.02 | 1.04 | 0.02 | 0.07 |
| 7020538 | MR I | 0.97 | 0.94 | 1.03 | | 0.03 | |
| 7020551 | MR I | 2.02 | 1.87 | 1.08 | | 0.15 | |
| WT P2 | WT | 11.37 | 7.52 | 1.51 | 1.48 | 3.86 | 3.81 |
| 305 | WT | 9.99 | 6.90 | 1.45 | | 3.09 | |
| 2176 | WT | 14.06 | 9.57 | 1.47 | | 4.49 | |

FIGS. 3 and 4 show the different reaction kinetics of the conversion of S-2288, i.e. the amidolytic activity of FSAP. FIG. 3 shows the reaction kinetics found for a plasma sample of a non-carrier of the MR I mutation without and with addition of aprotinin (0.036 and 0.055 KIU/ml final aprotinin concentration). FIG. 4 shows the reaction kinetics found for a plasma sample of a heterozygous carrier of the FSAP MR I variant without and with addition of aprotinin (0.036 and 0.055 KIU/ml final aprotinin concentration). It is clearly evident that the amidolytic activity of FSAP in the sample of the non-carrier is inhibited considerably more strongly in the presence of aprotinin than is the amidolytic activity of FSAP in the sample of the heterozygous carrier.

EXAMPLE 3

Determination of the Change in the Amidolytic Activity of FSAP for the Low Molecular Weight Chromogenic Peptide Substrate S-2288 by Addition of a Differential Activity Modulator During the Reaction The microtiter plates used were the same as described in example 1. In each case 100 µl of a plasma sample to be determined were pipetted in a dilution of 1:15 in sample buffer (see example 1) into the wells. After incubation at +37° C. for one hour, unbound constituents were removed by washing three times as in example 1.

To determine the amidolytic activity of FSAP, at time $t_0$ in each case 80 µl of the chromogenic substrate S-2288 (1.5 mmol/L; Chromogenix Instrumentation Laboratory S.p.A., Milano, Italy) in a 50:50 mixture of test buffer I and test buffer II (see example 1 for test buffer I and II) were put into the MTP wells and incubated at +37° C. in a photometer. After about 60 minutes, aprotinin was added in a final concentration $v_{max\ activity\ modulator}$. Three independent measurements were carried out on the sample of the non-carrier of the FSAP MR I variant (wild-type sample; WT). Six independent measurements were carried out on the sample of the heterozygous carrier of the FSAP MR I variant (MR I). The averages (Av.) of $v_{max}$/$v_{max\ activity\ modulator}$ ($v_{max}$/$v_{maxA}$) and the standard deviations relating to the population (SD) were calculated. The negative control, i.e. addition of a corresponding volume of test buffer I and test buffer II in the ratio 50:50 without activity modulator afforded an Av. $v_{max}$/$v_{maxA}$ of 0.81 +/− 0.12.

A t-test was carried out in order to obtain an indication of the significance of the influence of an activity modulator. The t-test was based on the assumption of two samples with equal and unequal variance. A one-sided test (one tail) was carried out. This t-test shows that aprotinin, the monoclonal anti-FSAP antibody MAb 2004-151/013(2) (DSM ACC2726) and the monoclonal anti-FSAP antibody MAb 2004-98/016(3) reduce with appropriate significance the activity of the WT sample more than the MR I sample, so that the WT/MR I quotient is >1. The monoclonal anti-FSAP antibody MAb 1102/1189-2 (DSM ACC2454) by contrast enhances the activity of the WT sample more than the MR I sample, so that the WT/MR I quotient is <1. This is also the case with the monoclonal anti-FSAP antibody MAb 2004-35/05(1) (DSM ACC2674). Although the P-values in this case do not indicate any significance, they are comparatively small, and it can therefore be assumed that with a sufficient number of measurements, i.e. with a larger number of cases, the null hypothesis can be rejected. MAb 1102/1189-2 (DSM ACC2454) and MAb 2004-35/05(1) (DSM ACC2674) are thus likewise suitable activity modulators.

In contrast thereto, the monoclonal anti-FSAP antibodies MAb 1102/570-09 (DSM ACC2533, see EP 1 334 983 A2), MAb 2004-9/026(2) (DSM ACC2676, see EP 1 630 175 A1) and MAb 2004-34/08(2) (DSM ACC2725, see EP 1 630 175 A1) are, according to their WT/MR I quotients and their t-test values, unsuitable as activity modulators.

TABLE 3

| Activity modulator | WT Av. $v_{max}/v_{max\,A}$ | SD | MRI Av. $v_{max}/v_{max\,A}$ | SD | WT/MRI | P-value for equal variance | P-value for unequal variance |
|---|---|---|---|---|---|---|---|
| Aprotinin | 16.72 | 1.38 | 12.36 | 2.31 | 1.35 | 0.0331 | 0.0224 |
| MAb 1102/570-09 (DSM ACC2533) | 1.32 | 0.20 | 1.36 | 0.15 | 0.97 | 0.7947 | 0.8293 |
| MAb 1102/1189-2 (DSM ACC2454) | 0.72 | 0.03 | 0.78 | 0.04 | 0.92 | 0.0757 | 0.0625 |
| MAb 2004-9/026(2) (DSM ACC2676) | 0.71 | 0.05 | 0.76 | 0.03 | 0.93 | 0.1109 | 0.2555 |
| MAb 2004-35/05(1) (DSM ACC2674) | 0.71 | 0.07 | 0.87 | 0.19 | 0.82 | 0.2596 | 0.1531 |
| MAb 2004-34/08(2) (DSM ACC2725) | 0.74 | 0.05 | 0.77 | 0.06 | 0.95 | 0.4143 | 0.4229 |
| MAb 2004-151/013(2) (DSM ACC2726) | 0.95 | 0.04 | 0.80 | 0.05 | 1.19 | 0.0057 | 0.0119 |
| MAb 2004-98/016(3) | 0.94 | 0.05 | 0.77 | 0.06 | 1.23 | 0.0063 | 0.0109 |

The invention claimed is:

1. A method for identifying whether an individual shows heterozygous or homozygous expression of the Marburg I (MR I) variant of factor MI-activating protease (FSAP), comprising determining FSAP activity in a sample from the individual in the absence and in the presence of aprotinin, wherein aprotinin
    reduces FSAP activity, and
    reduces FSAP activity in samples from individuals with heterozygous or homozygous expression of the MR I variant of FSAP to a lesser extent than reduces FSAP activity in samples from individuals who do not express said MR I variant of FSAP.

2. The method of claim 1, wherein the extent of the change in FSAP activity is determined by:
    (a) determining FSAP activity in a first portion of the sample in the presence of the aprotinin;
    (b) determining FSAP activity in a second portion of the sample in the absence of the aprotinin; and
    (c) comparing the activity determined in part (a) to the activity determined in part (b).

3. The method of claim 2, wherein the activity determined in part (a) is compared to the activity determined in part (b) by calculating a quotient of the activity of part (a) and the activity of part (b).

4. The method of claim 1, wherein the extent of the change in FSAP activity is determined by:
    (a) determining FSAP activity in the sample in the absence of the aprotinin;
    (b) adding the aprotinin to the sample and re-determining the FSAP activity in the sample; and
    (c) comparing the activity determined in part (a) to the activity determined in part (b).

5. The method of claim 4, wherein the activity determined in part (a) is compared to the activity determined in part (b) by calculating a quotient of the activity of part (a) and the activity of part (b).

6. A method for identifying whether an individual shows heterozygous or homozygous expression of the Marburg I (MR I) variant of factor VII-activating protease (FSAP), comprising determining FSAP activity in a sample from the individual in the absence and in the presence of a polyclonal or monoclonal anti-FSAP antibody, wherein the antibody
    reduces FSAP activity, and
    reduces FSAP activity in samples from individuals with heterozygous or homozygous expression of the MR I variant of FSAP to a lesser extent than the antibody reduces FSAP activity in samples from individuals who do not express said MR I variant of FSAP.

7. The method of claim 6, wherein the anti-FSAP antibody is a monoclonal antibody produced by hybridoma cell line DSM ACC2726.

8. The method of claim 6, wherein the anti-FSAP antibody binds to an epitope of FSAP to which the monoclonal antibody produced by hybridoma cell line DSM ACC2726 also binds.

9. A method for identifying whether an individual shows heterozygous or homozygous expression of the Marburg I (MR I) variant of factor VII-activating protease (FSAP), comprising determining FSAP activity in a sample from the individual in the absence and in the presence of a monoclonal or polyclonal anti-FSAP antibody, wherein the antibody
    increases FSAP activity, and
    increases FSAP activity in samples from individuals with heterozygous or homozygous expression of the MR I variant of FSAP to a lesser extent than the antibody increases FSAP activity in samples from individuals who do not express said MR I variant of FSAP.

10. The method of claim 9, wherein the anti-FSAP antibody is a monoclonal antibody produced by hybridoma cell line DSM ACC2454 or DSM ACC2674.

11. The method of claim 9, wherein the anti-FSAP antibody binds to an epitope of FSAP to which one or both of the monoclonal antibodies produced by hybridoma cell lines DSM ACC2454 and DSM ACC2674 also binds.

12. The method of claim 6 or 9, wherein the extent of the change in FSAP activity is determined by:
    (a) determining FSAP activity in a first portion of the sample in the presence of the antibody;
    (b) determining FSAP activity in a second portion of the sample in the absence of the antibody; and
    (c) comparing the activity determined in part (a) to the activity determined in part (b).

13. The method of claim 12, wherein the activity determined in part (a) is compared to the activity determined in part (b) by calculating a quotient of the activity of part (a) and the activity of part (b).

14. The method of claim 6 or 9, wherein the extent of the change in FSAP activity is determined by:
    (a) determining FSAP activity in the sample in the absence of the antibody;
    (b) adding the antibody to the sample and re-determining the FSAP activity in the sample; and (c) comparing the activity determined in part (a) to the activity determined in part (b).

15. The method of claim 14, wherein the activity determined in part (a) is compared to the activity determined in part (b) by calculating a quotient of the activity of part (a) and the activity of part (b).

16. The method of claim 1, 6, or 9, wherein FSAP activity is determined by measuring the plasminogen activator activating activity of FSAP.

17. The method of claim 1, 6, or 9, wherein FSAP activity is determined by measuring the prourokinase activating activity of FSAP.

18. The method of claim 1, 6, or 9, wherein FSAP activity is determined by measuring the amidolytic activity of FSAP.

19. The method of claim 1, 6, or 9, wherein the activity of FSAP is determined by measuring reaction rate ($V_{max}$) of a substrate conversion.

* * * * *

UNITED STATES PATENT AND TRADEMARK OFFICE
CERTIFICATE OF CORRECTION

| | | |
|---|---|---|
| PATENT NO. | : 7,943,333 B2 | Page 1 of 1 |
| APPLICATION NO. | : 11/642747 | |
| DATED | : May 17, 2011 | |
| INVENTOR(S) | : Frank Vitzthum et al. | |

It is certified that error appears in the above-identified patent and that said Letters Patent is hereby corrected as shown below:

In Claim 1, col. 15, line 23, "MI-activating" should read --VII-activating--.

Signed and Sealed this
Thirteenth Day of September, 2011

David J. Kappos
*Director of the United States Patent and Trademark Office*